United States Patent
Bang et al.

(10) Patent No.: US 9,380,945 B2
(45) Date of Patent: Jul. 5, 2016

(54) METHOD AND APPARATUS FOR GENERATING A TEMPERATURE IMAGE

(71) Applicant: Samsung Electronics Co., Ltd., Suwon-si (KR)

(72) Inventors: Won-chul Bang, Seongnam-si (KR); Dong-geon Kong, Hwaseong-si (KR); Ki-wan Choi, Anyang-si (KR); Ji-young Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 117 days.

(21) Appl. No.: 14/161,928

(22) Filed: Jan. 23, 2014

(65) Prior Publication Data
US 2014/0206996 A1 Jul. 24, 2014

(30) Foreign Application Priority Data
Jan. 23, 2013 (KR) .................. 10-2013-0007653

(51) Int. Cl.
| | |
|---|---|
| *A61B 8/00* | (2006.01) |
| *A61B 5/01* | (2006.01) |
| *A61B 8/08* | (2006.01) |
| *G01S 7/52* | (2006.01) |
| *A61N 7/02* | (2006.01) |
| *A61B 5/00* | (2006.01) |
| *G01S 15/89* | (2006.01) |
| *A61B 17/00* | (2006.01) |
| *A61N 7/00* | (2006.01) |

(52) U.S. Cl.
CPC .............. *A61B 5/015* (2013.01); *A61B 5/4848* (2013.01); *A61B 8/483* (2013.01); *A61B 8/5223* (2013.01); *A61N 7/02* (2013.01); *G01S 7/52036* (2013.01); *G01S 7/52071* (2013.01); *G01S 7/52085* (2013.01); *A61B 5/0037* (2013.01); *A61B 8/44* (2013.01); *A61B 2017/00084* (2013.01); *A61B 2017/00106* (2013.01); *A61N 2007/0095* (2013.01); *G01S 15/8993* (2013.01)

(58) Field of Classification Search
CPC ............ A61B 8/00; A61B 8/08; A61B 8/483; A61B 5/4848; A61B 2019/5276
See application file for complete search history.

(56) References Cited

U.S. PATENT DOCUMENTS

| | | | |
|---|---|---|---|
| 8,226,559 B2 | 7/2012 | Liu et al. | |
| 8,852,103 B2 * | 10/2014 | Rothberg et al. | 600/438 |
| 2011/0306881 A1 | 12/2011 | Liu et al. | |

FOREIGN PATENT DOCUMENTS

| | | |
|---|---|---|
| JP | 2000-300536 | 10/2000 |
| JP | 2001-190587 | 7/2001 |
| KR | 10-2012-0081384 | 7/2012 |

* cited by examiner

*Primary Examiner* — Joel Lamprecht
(74) *Attorney, Agent, or Firm* — NSIP Law

(57) ABSTRACT

Disclosed is a method and apparatus of generating a temperature image during ultrasonic treatment, the method including setting a first plane indicating a heating region where ultrasonic waves for treatment are irradiated and setting a second plane indicating a protective region around the heating region; irradiating the first plane with ultrasonic waves for diagnosis at a first frame rate, and irradiating the second plane with the ultrasonic waves for diagnosis at a second frame rate, the second frame rate being lower than the first frame rate; and generating the temperature image using frame images acquired from irradiating the ultrasonic waves for diagnosis.

20 Claims, 10 Drawing Sheets

METHOD AND APPARATUS FOR GENERATING A TEMPERATURE IMAGE

CROSS-REFERENCE TO RELATED APPLICATIONS

This application claims the benefit under 35 U.S.C. §119 (a) of Korean Patent Application No. 10-2013-0007653, filed on Jan. 23, 2013, in the Korean Intellectual Property Office, the entire disclosure of which is incorporated herein by reference for all purposes.

BACKGROUND

1. Field

The following description relates to methods and apparatuses for generating a temperature image, and ultrasound systems including the apparatus.

2. Description of Related Art

Topical treatments applied to a tumor have been developed from invasive surgeries, such as an abdominal surgical operation, to minimally invasive surgeries. Non-invasive surgerical techniques and procedures are also being developed, and, a gamma knife, a cyber knife, a High Intensity Focused Ultrasound (HIFU) knife, and so forth are used in such procedures. Among these procedures, the HIFU knife is widely used in therapy that is harmless to the human body and is eco-friendly due to the use of ultrasonic waves.

HIFU therapy using an HIFU knife is a surgery method for removing and healing a tumor affected area by focusing and irradiating HIFU waves onto a tumor to cause focal destruction or necrosis of tumor tissue. HIFU therapy does not treat a two-dimensional plane, but treats a three-dimensional volume, and thus, temperature monitoring of the three-dimensional volume is desired.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect there is provided a method of generating a temperature image during ultrasonic treatment, the method including setting a first plane indicating a heating region where ultrasonic waves for treatment are irradiated and setting a second plane indicating a protective region around the heating region; irradiating the first plane with ultrasonic waves for diagnosis at a first frame rate, and irradiating the second plane with the ultrasonic waves for diagnosis at a second frame rate, the second frame rate being lower than the first frame rate; and generating the temperature image using frame images acquired from irradiating the ultrasonic waves for diagnosis.

The generating of the temperature image may include generating the temperature image by comparing a reference frame indicating a frame image acquired before irradiating the ultrasonic waves for treatment, with a current frame indicating a frame image acquired while or after irradiating the ultrasonic waves for treatment.

The method may include displaying the generated temperature image on a set plane including the first plane and the second plane.

The irradiating of the ultrasonic waves for diagnosis may include time-dividing and irradiating the first plane and the second plane with the ultrasonic waves for diagnosis.

The ultrasonic waves for diagnosis may be irradiated onto the second plane at a third frame rate that is higher than the second frame rate in response to a temperature change on the second plane being greater than a threshold.

The method may include acquiring three-dimensional volume data for an organ within a body; setting a plane of interest to be observed during ultrasonic treatment; and extracting a region corresponding to the plane of interest from the three-dimensional volume data, wherein the first plane and the second plane are set on the extracted region.

The temperature image corresponding to the plane of interest may be displayed on the three-dimensional volume data.

Setting the plane of interest may include setting a plurality of planes of interest to be observed during ultrasonic treatment.

The ultrasonic waves for treatment and the ultrasonic waves for diagnosis may be irradiated from a single transducer.

In another aspect there is provided a method of generating a temperature image during ultrasonic treatment, the method including acquiring three-dimensional volume data for an organ within a body; setting a plane of interest to be observed at the time of the ultrasonic treatment; extracting a region corresponding to the plane of interest from the three-dimensional volume data; and generating the temperature image using frame images acquired from irradiating ultrasonic waves for diagnosis on the plane of interest.

The method may include displaying the temperature image corresponding to the plane of interest on the three-dimensional volume data.

In another aspect there is provided an apparatus for generating a temperature image during ultrasonic treatment, the apparatus including a region setter configured to set a first plane indicating a heating region where ultrasonic waves for treatment are irradiated, and to set a second plane indicating a protective region around the heating region; an irradiation controller configured to irradiate the first plane with ultrasonic waves for diagnosis at a first frame rate, and to irradiate the second plane with the ultrasonic waves for diagnosis at a second frame rate, the second frame rate being lower than the first frame rate; and a temperature image generator configured to generate the temperature image using frame images acquired from irradiating the ultrasonic waves for diagnosis.

The temperature image generator may be further configured to generate the temperature image by comparing a reference frame indicating a frame image acquired before irradiating the ultrasonic waves for treatment, with a current frame indicating a frame image acquired while or after irradiating the ultrasonic waves for treatment.

The apparatus may include a display controller configured to display the generated temperature image on a set plane including the first plane and the second plane.

The irradiation controller may time-divide and irradiate the first plane and the second plane with the ultrasonic waves for diagnosis.

The irradiation controller may be further configured to irradiate the second plane with the ultrasonic waves for diagnosis at a third frame rate that is higher than the second frame rate in response to a temperature change on the second plane being greater than a threshold.

In another aspect there is provided an apparatus for generating a temperature image during ultrasonic treatment, the apparatus including a three-dimensional volume data acquirer configured to acquire three-dimensional volume data for an organ within a body; a plane of interest setter configured to set a plane of interest intended to be observed at the time of the ultrasonic treatment; an extractor configured to extract a region corresponding to the set plane of interest from the three-dimensional volume data; and a temperature image generator configured to generate the temperature image using frame images acquired from irradiating the ultrasonic waves for diagnosis on the plane of interest.

The apparatus may include a display controller configured to display the temperature image corresponding to the plane of interest on the three-dimensional volume data.

In another aspect there is provided an ultrasonic apparatus including a temperature image generation device to produces a temperature image during ultrasonic treatment, the ultrasonic apparatus including an ultrasonic treatment device configured to generate ultrasonic waves to irradiate a treatment region of an organ in a body and heat a lesion for treatment; an ultrasound diagnosis device configured to generate ultrasound waves to irradiate the treatment region and a region surrounding the treatment region, and to output reflected waves of the ultrasonic waves for diagnosis; and the temperature image generation device configured to set a first plane indicating a heating region where the ultrasonic waves for treatment are irradiated and to set a second plane that indicates a protective region around the heating region, to irradiate the first plane with the ultrasonic waves at a first frame rate for diagnosis, to irradiate the second plane with the ultrasonic waves at a second frame rate, the second frame rate being lower than the first frame rate, and to generate the temperature image using frame images acquired from reflected waves output by the ultrasonic diagnosis device.

The apparatus may include a display device configured to display the generated temperature image on a set plane including the first plane and the second plane, wherein the display device is controlled by the temperature image generation device.

Other features and aspects will be apparent from the following detailed description, the drawings, and the claims.

Figure 1:
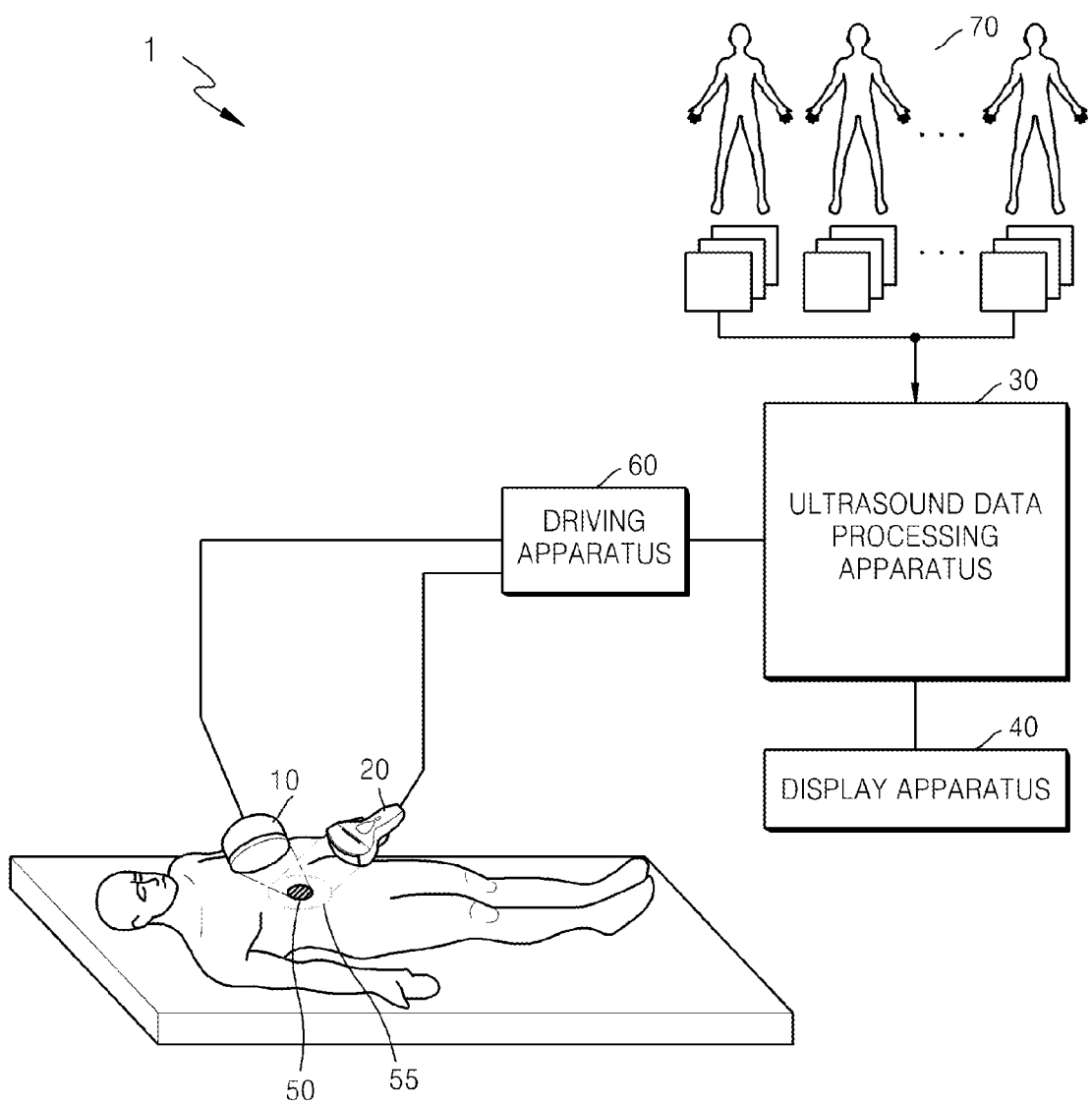
FIG. 1 is a diagram illustrating an example of an ultrasound system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating an example of an ultrasound system 1. Referring to FIG. 1, the ultrasound system 1 includes an ultrasound treatment device 10, an ultrasound diagnosis device 20, an ultrasound data processing device 30, a display device 40, and a driving device 60. In the ultrasound system 1 shown in FIG. 1, only components related to the present example are shown. Thus, those skilled in the art may understand that general components except for components illustrated in FIG. 1 may be further included. For example, the ultrasound system 1 may include an interface unit (not illustrated). The interface unit may be responsible for inputting and outputting input information regarding a user and an image. The interface unit may include a network module for connection to a network and a universal serial bus (USB) host module for forming a data transfer channel with a mobile storage medium, depending on a function of the ultrasound system 1. In addition, the interface unit may include an input/output device such as a mouse, a keyboard, a touch screen, a monitor, a speaker, and a software module for running the input/output device. In addition, the ultrasound system 1 may further include a storage unit (not illustrated) that stores models that are described below. The storage unit may include, for example, a hard disk drive (HDD), a read only memory (ROM), a random access memory (RAM), a flash memory, or a memory card as an ordinary storage medium. In addition, external medical images 70 captured by medical experts for the diagnosis of patients may be input to the ultrasound data processing device 30.

The display device 40 may be implemented as a liquid crystal display (LCD), a light-emitting diode (LED) display, a plasma display panel (PDP), a screen, a terminal, and the like. A screen may be a physical structure that includes one or more hardware components that provide the ability to render a user interface and/or receive user input. The screen can encompass any combination of display region, gesture capture region, a touch sensitive display, and/or a configurable area. The screen can be embedded in the hardware or may be an external peripheral device that may be attached and detached from the apparatus. The display device 40 may be a single-screen or a multi-screen display. A single physical screen can include multiple displays that are managed as separate logical displays permitting different content to be displayed on separate displays although part of the same physical screen.

When a tumor in a patient needs to be treated, the ultrasound treatment device 10 in the ultrasound system 1 is used to apply heat by irradiating an ultrasound wave for treatment onto a treatment part 50 of the tumor. The ultrasound diagnosis device 20 irradiates an ultrasound wave for diagnosis onto a surrounding part 55, which includes the treatment part 50 and receives reflected waves of the irradiated ultrasound wave. The ultrasound system 1 converts the received reflected waves to echo signals, acquires ultrasound images based on the echo signals, and diagnoses whether the therapy has been completed. The heat causes focal destruction or necrosis of tissue in the treatment part 50. The ultrasound system 1 treats the treatment part 50 by using the ultrasound treatment device 10 for irradiating the ultrasound wave onto the treatment part 50, such as, for example, a portion of the tumor, in the body of the patient. The result of the treatment, including but not limited to, a temperature of the treatment part 50, is monitored by the ultrasound diagnosis device 20 for irradiating the ultrasound wave for diagnosis onto the surrounding part 55.

The ultrasound treatment device 10 may be called a treatment probe. The ultrasound treatment device 10 may irradiate the ultrasound wave for treatment onto various parts of a patient while moving under the control of the driving device 60. Alternatively, the ultrasound treatment device 10 may irradiate the ultrasound wave for treatment onto various parts of a patient by changing a focal position where the ultrasound wave for treatment is irradiated and the position of the ultrasound treatment device 10 may remain fixed. The ultrasound treatment device 10 generates the ultrasound wave for treatment and irradiates the ultrasound wave for treatment onto local tissue of a patient. High Intensity Focused Ultrasound (HIFU) having enough energy to cause necrosis of a tumor in the body of a patient may be used as the ultrasound wave for treatment. The ultrasound treatment device 10 corresponds to a device for irradiating HIFU waves generally known as ultrasound waves for treatment. Since the HIFU is well known to one of ordinary skill in the art, its detailed description is omitted. It will be understood by one of ordinary skill in the art that the ultrasound treatment device 10 is not limited to the device for irradiating HIFU waves and any device may be included in the scope of the ultrasound treatment device 10 as long as it is similar to the device for irradiating HIFU waves.

Figure 2:
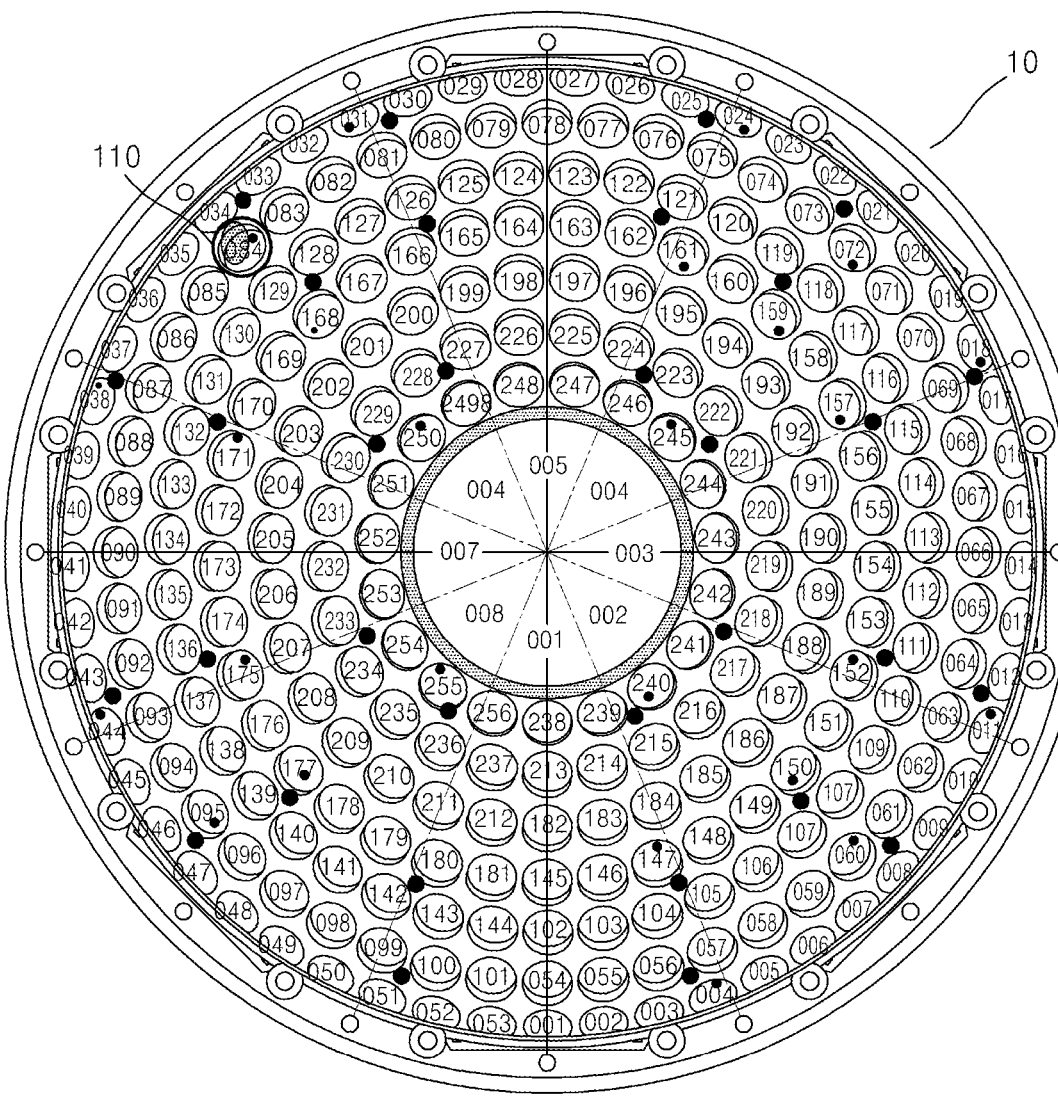
FIG. 2 is a diagram illustrating an example of an ultrasound treatment device

The method of changing a focal position at which the ultrasound wave for treatment is irradiated by the ultrasound treatment device 10 may use a phase array (PA) method. The PA method is performed by the ultrasound treatment device 10 shown in FIG. 2, which, illustrates an example of an ultrasound treatment device including a plurality of elements 110. As shown in FIG. 2, a plurality of elements 110 may individually irradiate an ultrasound wave when a signal is received from the driving device 60 and may have differently timings for irradiating the ultrasound waves. The individual irradiation of an ultrasound wave by the plurality of elements 110 may enable the ultrasound treatment device 10 to irradiate the ultrasound wave based on movements of a lesion even when the position of the ultrasound treatment device 10 is fixed. Thus, the PA method has the same effect as a method of irradiating an ultrasound wave while the ultrasound treatment device 10 is physically moving. In addition, although the ultrasound treatment device 10 shown in FIG. 2 is formed to have a circular shape in FIG. 2, the ultrasound treatment device 10 may be formed to have various shapes, such as, for example, a quadilateral, a triangle.

The ultrasound diagnosis device 20 may be referred to as a diagnosis probe. The ultrasound diagnosis device 20 irradiates the ultrasound wave for diagnosis towards the surrounding part 55 under control of the driving device 60. The observed part 55 may be lager than or the same as the treatment part 50. The ultrasound diagnosis device 20 receives ultrasound waves reflected from the diagnosis ultrasound-irradiated portion. The ultrasound diagnosis device 20 may include a piezoelectric transducer. When an ultrasound wave in a range of 2 MHz to about 18 MHz is propagated to a predetermined part in the body of a patient from the ultrasound diagnosis device 20, the ultrasound wave is partially reflected from layers between different tissues. The ultrasound wave is reflected from places in the body in which density changes, for example, blood cells in blood plasma and small tissue in organs. These reflected ultrasound waves cause the piezoelectric transducer to vibrate and output electrical pulses in response to the vibration. In the present non-exhaustive example, echo signals converted from reflected waves received by the ultrasound diagnosis device 20 are used to monitor other characteristics, such as, for example, a temperature change of the observed part. The echo signals may be used to monitor a temperature change at the observed part in addition to the generation of an ultrasound diagnosis image. A method of monitoring a temperature change at the observed part is described below. The ultrasound diagnosis device 20 may also be implemented at a fixed position, and may be configured to have a size capable of accommodating a predetermined internal organ including the treatment part 50.

The ultrasound treatment device 10 and the ultrasound diagnosis device 20 are shown as independent apparatuses, the present disclosure is not limited thereto. The ultrasound treatment device 10 and the ultrasound diagnosis device 20 may be implemented as individual modules in a single device or implemented as an actual single device. In addition, the ultrasound treatment device 10 and the ultrasound diagnosis device 20 are not limited to being singular, and there may be a plurality of ultrasound treatment devices 10 and a plurality of ultrasound diagnosis devices 20. The treatment ultrasound apparatus 10 and the diagnosis ultrasound apparatus 20 may irradiate ultrasound in any direction. For example, while the ultrasound treatment device 10 and the ultrasound diagnosis device 20 are shown irradiating ultrasound waves downwards from above the body of a patient in FIG. 1, a method of irradiating ultrasound waves in various other directions, for example, a method of irradiating ultrasound waves upwards from below the body of a patient, may be implemented.

The driving device 60 controls positions of the ultrasound treatment device 10 and the ultrasound diagnosis device 20. The driving device 60 receives position information of the treatment part 50 from the ultrasound data processing device 30 and controls a position of the ultrasound treatment device 10 so that the ultrasound treatment device 10 correctly irradiates the ultrasound wave for the treatment on the treatment part 50. The driving device 60 receives position information of the observed part from the ultrasound data processing device 30 and controls a position of the ultrasound diagnosis device 20 so that the ultrasound diagnosis device 20 correctly irradiates the ultrasound wave for diagnosis on the observed part and receives reflected ultrasound wave for the diagnosis.

As described above, the ultrasound system 1 also monitors a temperature change at the observed part using the ultrasound diagnosis device 20. In a case of an ultrasound therapy using the ultrasound wave for the treatment, such as the HIFU procedure, when the HIFU wave arrives at a portion of a tumor, a temperature of this tumor portion may instantaneously increase to more than 70° C. due to heat energy generated by the HIFU wave. Tissue destruction may occur within about 110 msec at a temperature of about 60° C. This high temperature causes coagulative necrosis of tissue and blood vessels in the tumor portion. By monitoring a temperature change at the observed part in real-time, it may be determined whether a therapy is to be continued or has been completed, so that an ultrasound therapy may be efficiently performed.

The ultrasound data processing device 30 generates a temperature image showing a temperature change of the observed part of the body of a patent at the time of the ultrasound treatment. The ultrasound data processing device 30 acquires three-dimensional volume data, and if a desired plane of interest is designated, the ultrasound data processing device 30 extracts data of the designated plane of interest and generates the observed temperature image of the plane of interest. The ultrasound data processing device 30 may be referred to as an apparatus for generating a temperature image.

The ultrasound data processing device 30 controls irradiation of ultrasound waves for diagnosis at a high frame rate so that more frame images may be acquired for a treatment region. The treatment region may be a region having a large temperature change, for example, the region corresponding to the treatment part 50 illustrated in FIG. 1. The ultrasound data processing device 30 also controls irradiation of ultrasound waves for diagnosis at a low frame rate so that less frame images may be acquired in a region around the treatment part 50 where a large temperature change may not be present. Such a region may be a surrounding part 55 of the treatment part 50 illustrated in FIG. 1. Thus, a doctor or expert who gives medical treatment may divide and designate the observed part, or the observed part may be automatically designated by the ultrasound system 1 so that the three-dimensional temperature monitoring needed at the time of the HIFU treatment for treating the three-dimensional volume may be performed in real time.

The ultrasound data processing device 30 may control the frame rate of the ultrasound wave for diagnosis to efficiently use the ultrasound wave for diagnosis or the resources of the ultrasound wave diagnosis device 20 at the time of the ultrasound treatment so that the temperature change may be monitored. Furthermore, the ultrasound data processing device 30 may extract data of a plurality of planes of interest from the three-dimensional volume data and generate a temperature image for the data of the extracted region, thereby reducing resource consumption and the number of calculations used in generating the temperature images for the entire three-dimensional volume data.

Figure 3:
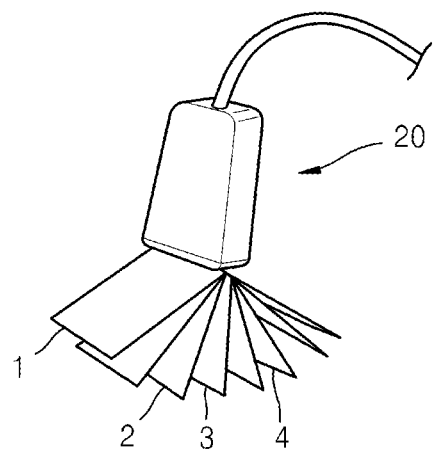
FIG. 3 is a diagram illustrating an example of irradiation using an ultrasound diagnosis device.
Figure 4:
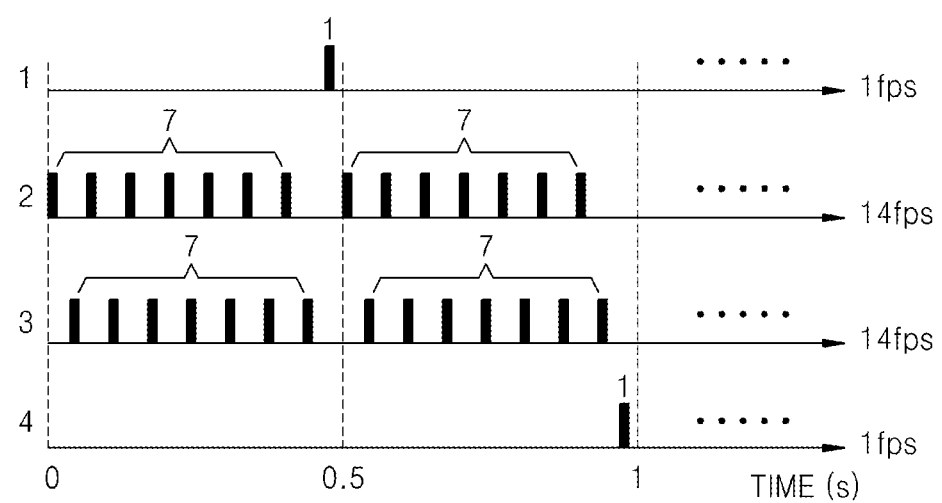
FIG. 4 is a diagram illustrating an example of time division irradiation on a heating area and a protective area using the ultrasound diagnosis device illustrated in FIG. 3.

FIG. 3 is a diagram illustrating an example of irradiation using an ultrasound diagnosis device 20. FIG. 4 is a diagram illustrating an example of time division irradiation onto a heating area and a protective area using an ultrasound diagnosis device illustrated in FIG. 3.

Referring to FIGS. 1, 3 and 4, the ultrasound diagnosis device 20 irradiates the ultrasound wave toward the part of the body under control of the driving device 60. The ultrasound diagnosis device 20 may irradiate the ultrasound wave toward the part of the body in a plurality of irradiated planes. Here, irradiated plane 1 and irradiated plane 4 are protective observation planes, and irradiated planes 2 and 3 are heat treatment observation planes. As illustrated in FIG. 1, irradiated planes 2 and 3 may be a region corresponding to the treatment part 50, and irradiated planes 1 and 4 are may be a region of the surrounding part 55, except for the treatment part 50. In the present non-exhaustive examples, the ultrasound treatment device 10 divides the body of a patient into a heating region to be heated and a protective region around the heating region. The present disclosure, however, is not limited thereto, and the body of the patient may also be divided into a region to be observed by a doctor performing ultrasound treatment, and a surrounding region.

As illustrated in FIG. 4, the ultrasound diagnosis device 20 time-divides the entire irradiated region and irradiates the ultrasound wave for diagnosis. If the maximum frame rate, which may be obtained by irradiating the ultrasound wave for diagnosis onto the irradiated plane, is 30 frames per second (fps), each irradiated plane (1 to 4) is time-divided for irradiation. Frame image no. 1 is obtained by irradiating the irradiated plane 2 with the ultrasound wave for diagnosis, frame image no. 2 is obtained by irradiating the irradiated plane 3 with the ultrasound wave for diagnosis. In such a manner, 30 frame images are obtained on each irradiated plane during 1 second.

The ultrasound wave for diagnosis is irradiated onto the irradiated plane 2, which is the heating region, to obtain 14 frame images in one second, and the ultrasound wave for diagnosis is irradiated onto the irradiated plane 3, which is the heating region, to obtain 14 frame images in one second. The ultrasound wave is irradiated onto the irradiated planes 1 and 4, which are protective regions, to acquire one frame image in one second. A total of 30 frames may be acquired in 1 second. A large number of frame images are acquired from the heating region having a relatively large temperature change so as to generate a temperature image showing a temperature change in the heating region. Only a small number of frame images are acquired from the protective region having a relatively small temperature change so as to generate a temperature image showing a temperature change in the protective region. The frame rate allocated to irradiated planes with respect to the heating region and irradiated planes with respect to the protective region is not fixed, and may change. For example, when there is a significant temperature change in the irradiated plane 1, which is the protective region, if the frame rate allocated to the irradiated plane 1 is 1 fps, the frame rate may be raised up to 14 fps.

Figure 5:
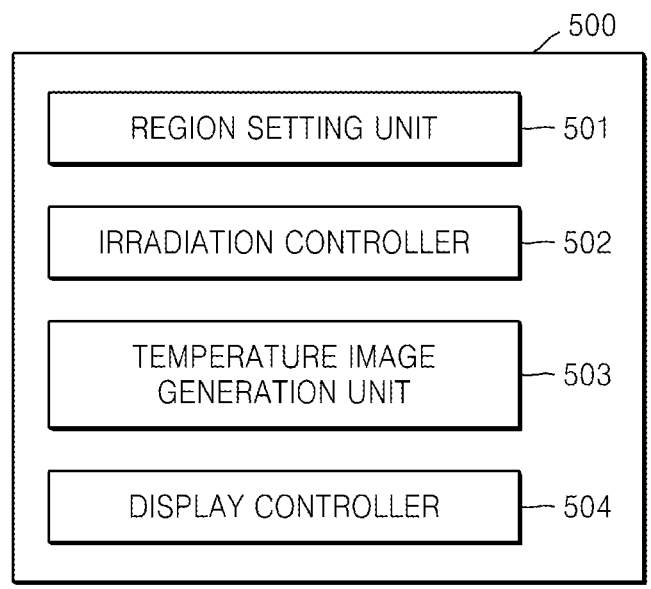
FIG. 5 is a diagram illustrating an example of a temperature image generation apparatus.

FIG. 5 is a diagram illustrating an example of a temperature image generation apparatus 500.

Referring to FIG. 5, the temperature image generation apparatus 500 includes a region setting unit 501, an irradiation controller 502, a temperature image generation apparatus 503, and a display controller 504. The temperature image generation apparatus 500 may be a part of the ultrasonic data processing device 30 illustrated in FIG. 1.

The region setting unit 501 sets a first plane indicating the heating region onto which the ultrasound wave for treatment is irradiated, and a second plane indicating the surrounding protective region. Here, each plane setting may be set in the ultrasound system 1 or the temperature image generation apparatus 500 as default. The plane setting may also be set arbitrarily by a person performing the ultrasonic treatment. For example, if the region, which the ultrasound wave for treatment is irradiated, is determined in the ultrasound system 1, the region may be set as a first plane, and the region around the first plane may be set as a second plane. Alternatively, the person performing the ultrasonic treatment may set the observed region for heating treatment as the first plane and may set the protective observed region as the second plane.

The irradiation controller 502 irradiates the first plane with the ultrasonic waves at the first frame rate and irradiates the second plane with the ultrasonic waves at the second frame rate that is lower than the first frame rate. The irradiation controller 502 distributes allocated maximum resources of the ultrasonic waves for diagnosis so that ultrasonic waves for diagnosis may be irradiated from the first plane to obtain more frame images and ultrasonic waves for diagnosis are irradiated from the second plane to obtain less frame images. The ultrasonic waves for diagnosis are irradiated onto the plane at their corresponding frame rate through the driving device 60 illustrated in FIG. 1 according to the frame rate control command of the irradiation controller 502.

The temperature image generation apparatus 503 generates a temperature image using obtained frame images. The temperature image generation apparatus 503 receives echo signals reflected by the irradiated ultrasonic waves for diagnosis to generate frame images, and generates a temperature image using the frame images. The temperature image generation apparatus 503 compares a reference frame, which is a frame image acquired before ultrasonic waves for treatment are irradiated, and a current frame, which is acquired while irradiating the ultrasonic waves for treatment or after irradiating the ultrasonic waves for treatment to generate a temperature image. The process of generating a temperature image by the temperature image generation apparatus 503 is described in detail below.

The reflected ultrasonic waves for diagnosis are received by the ultrasonic diagnosis device 20. The received reflected ultrasonic waves for diagnosis are converted into echo signals. The echo signals mean beamformed ultrasonic radio frequency (RF) signals or signals capable of distinguishing anatomical information of a medium such as a b-mode image and extracting temperature-related parameters through processing.

At the point of time when the ultrasonic treatment device 10 irradiates ultrasonic waves for treatment onto the treatment part 50, the ultrasonic diagnosis device 20 receives echo signals that are generated by converting the reflected ultrasonic waves, which were irradiated by the ultrasonic diagnosis device 20 onto the observed part. The ultrasonic diagnosis device 20 generates the current frame indicating the image of the observed part at the current point of time by using the received echo signals. The current frame includes the information regarding the location and temperature of the observed part. An example of the current frame with different brightness is a B-mode image. The B-mode image refers to the image of echo signals, which are generated by converting the reflected ultrasonic waves for diagnosis, indicated by the difference of brightness. Furthermore, the current frame may be a beamformed radio frequency (RF) signal. The RF signal is a signal that has maintained the signal waveform of the ultrasonic frequency band.

The reference frame is generated to include temperature information regarding the observed part before the ultrasonic treatment device 10 irradiates the treatment part 50 with the ultrasonic waves for treatment. The reference frame is generated to observe the relative temperature change before and after the ultrasonic waves for treatment are irradiated onto the treatment part 50.

The temperature image generation apparatus 503 extracts temperature-related parameters from the reference frame and the current frame. The temperature image for the current frame based on the temperature change of the observed part shown on the reference frame and the observed part shown on the current frame is generated by extracting temperature-related parameters. The temperature image for the current frame may include images, such as, for example, an image that displays the physical quantity proportional to the temperature, an image that displays relative temperature changes of the observed part shown on the reference frame and the observed part shown on the current frame, and an image that displays the absolute temperature value of the observed part shown on the current frame. The methods of extracting temperature-related parameters includes, but is not limited to, a change in backscattered energy (CBE) scheme, an echo-shift (ES) scheme, a B/A change calculation scheme, and a combination thereof.

The method of extracting temperature-related parameters in a CBE scheme is described below. Echo signals that constitute the reference frame are compared with echo signals that constitute the current frame, and the amplitude-changed portion is detected from the echo signals that constitute the current frame. The temperature change corresponding to the level of the detected amplitude change is detected from the mapping table stored in a storage unit (not shown). The temperature image for the current frame corresponding to the relative temperature change of the observed parts shown on the reference frame and the current frame is generated using the detected temperature change value. The mapping table is composed of change values of amplitudes of a plurality of echo signals that have been predetermined as changeable by reflected waves of ultrasonic waves for diagnosis, and temperature change values mapped to the respective change values of the amplitudes. In the mapping table, a temperature change value mapped to an amplitude change value denotes a temperature change value of the treatment part 50, which is expected from the amplitude change value. Generally, the CBE scheme is useful in measuring the temperature in a high temperature range of between about 36° C. and about 58° C.

The method of extracting temperature-related parameters in an ES scheme is described below. Echo signals from the reference frame are compared with echo signals from the current frame, and the part where the speed of the echo signals has been changed, that is, the part where a delay has occurred in the echo signals, is detected. Differentiation according to distance is performed so as to calculate the variation of the delay. The temperature change corresponding to the variation of the delay of the detected echo signals is detected from the mapping table stored in the storage unit (not shown). The temperature image for the current frame corresponding to the relative temperature change of the observed parts shown on the reference frame and the current frame is generated using the detected temperature change value. The mapping table may be acquired by considering rate change and thermal expansion, etc. in the tissue according to the temperature. In the mapping table, the temperature change value mapped to the variation value of the delay of one echo signal denotes a temperature change value of the treatment part 50 that is expected from the variation value of the delay of the each signal. Generally, the ES scheme is useful in measuring the temperature in a low temperature range of between about 36° C. and 43° C.

The method of extracting temperature-related parameters in a scheme of extracting a change of B/A is described below. A B/A value indicates a nonlinearity characteristic of the echo signal rate that is changed according to the temperature of the observed part onto which the ultrasonic wave for diagnosis is irradiated. B/A has been described in "Estimation of Temperature Distribution in Biological Tissue by Acoustic Nonlinearity Parameter; Zhang, D., X. Z. Liu, Gong, X. F; AIP Conference Proceedings; 2006, Vol. 838 Issue 1, p. 341. A B/A value of echo signals that constitute the reference frame is compared with a B/A value of echo signals that constitute the current frame, and a part where the B/A value has been changed is detected. The temperature change corresponding to the detected B/A change value of the echo signal is detected from the mapping table stored in the storage unit (not shown). The temperature image for the current frame corresponding to the relative temperature change of the observed parts shown on the reference frame and the current frame is generated using the detected temperature change value. The mapping table is composed of B/A change values of a plurality of echo signals that have been predetermined by irradiation of ultrasonic waves for diagnosis, and temperature change values mapped to the respective B/A change values. In the mapping table, the temperature change value mapped to the B/A change value of one echo signal denotes the temperature change value of the treatment part 50 that is expected from the B/A change value of the echo signal.

The image indicating the absolute temperature value of the observed part shown on the current frame denotes an image accurately indicating the temperature of the observed part shown on the current frame. Generally, before the ultrasonic treatment device 10 irradiates ultrasonic waves for treatment, the temperature of the observed part represents a temperature corresponding to a general body temperature. Temperature-related parameters are extracted, and the temperature increase value of the observed part shown on the current frame relative to the observed part shown on the reference frame is added to the patient's body temperature using the extracted parameters so as to generate an image indicating the absolute temperature value. The method of extracting temperature-related parameters has been explained above in the method of generating a relative temperature image.

The image indicating the physical quantity proportional to the temperature means a temperature image generated using the variation of the relay, the change of the amplitude, or B/A value of echo signals that constitute the reference frame and echo signals that constitute the current frame. Generally, these values are proportional to the temperature, and thus the information regarding the temperature change may be recognized by displaying the physical quantity as itself.

The temperature image generation apparatus 503 generates a completed temperature image showing the temperature change of the observed part composed of a first plane including the protective region and a second plane including the heating region according to various standards using the temperature image for the current frame.

The display controller 504 displays a temperature image generated by the temperature image generation unit 503 on the display device 40. The display controller 504 displays a temperature image generated on a region set by the region setting unit 501, that is, the region including the first plane and the second plane.

Figure 6:
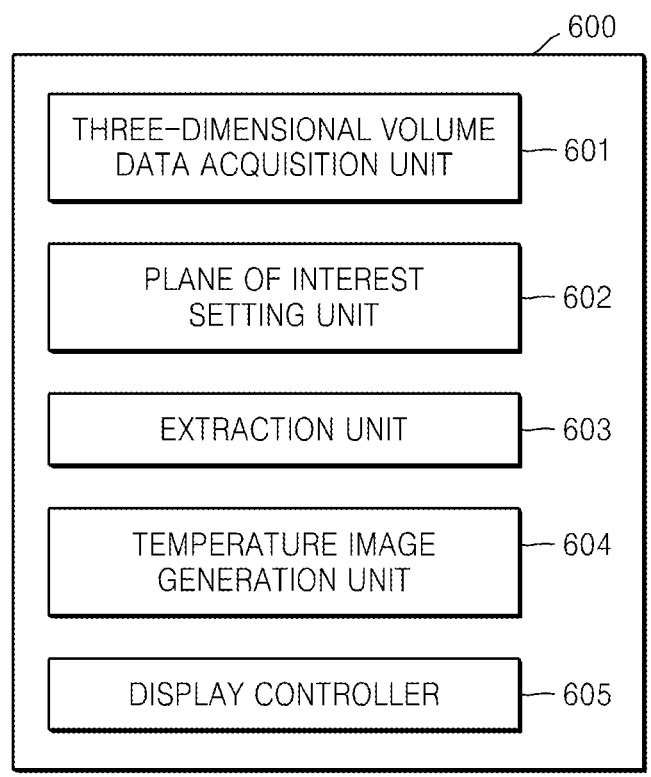
FIG. 6 is a diagram illustrating an example of a temperature image generation apparatus.

FIG. 6 is a diagram illustrating an example of a temperature image generation apparatus 600. Referring to FIG. 6, the temperature image generation apparatus 600 may include a three-dimensional volume data acquisition unit 601, a plane of interest setting unit 602, an extraction unit 603, a temperature image generation unit 604, and a display controller 605. The description of the same components included in the temperature image generation apparatus 500 illustrated in FIG. 5 is also applicable to the components shown in FIG. 6, and thus will not be repeated here.

Figure 9A:
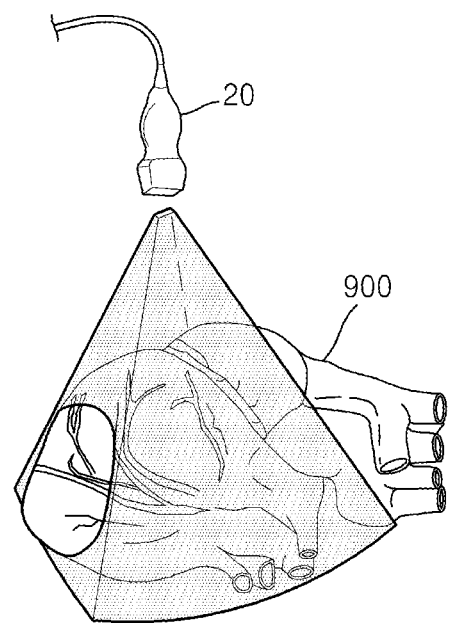
FIGS. 9A to 9E are diagrams illustrating examples of a method of generating a temperature image.

The three-dimensional volume data acquisition unit 610 acquires three-dimensional volume data for an organ within the patient's body. FIG. 9A illustrates an example of an image including three-dimensional data for an organ 900. Here, the three-dimensional volume data may be an image captured by a medical expert for patient diagnosis in order to analyze the shape, size, or other features of organs of various individuals, for example, an external medical image 70 illustrated in FIG. 1. The three-dimensional volume data may be a three-dimensional image such as, for example, a computed tomography (CT), magnetic resonance (MR), or ultrasonic image. A plurality of two-dimensional images may be input so as to reconfigure three-dimensional volume data.

Figure 9B:
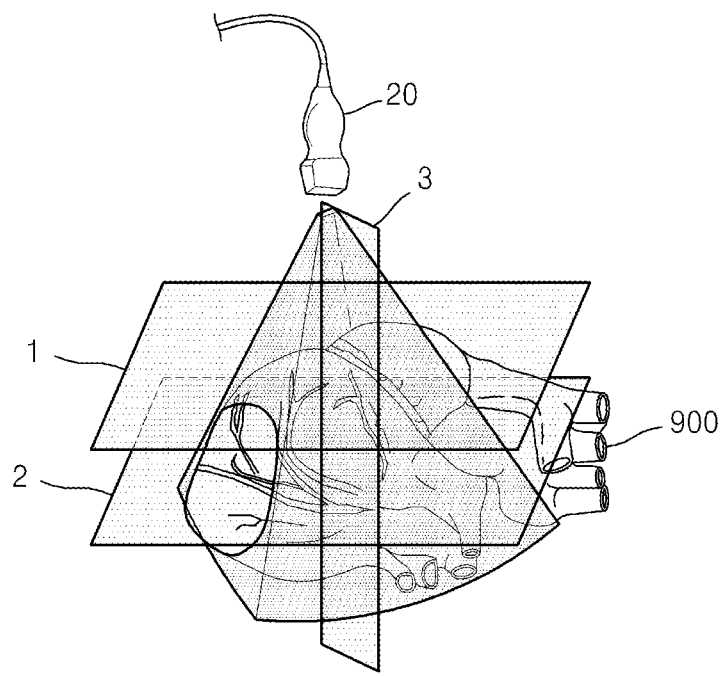

The plane of interest setting unit 602 sets the plane of interest intended to be observed at the time of ultrasonic wave treatment. FIG. 9B illustrates cross-sections 1 to 3 of an organ 900, and ultrasonic waves may be irradiated onto a cross-section through the ultrasonic diagnosis device 20. The ultrasonic waves for diagnosis are irradiated onto a cross-section by a combination of elements that constitute the transducer (not shown) of the ultrasonic diagnosis device 20, and a selective operation. Here, the plane of interest may be automatically set ultrasonic system 1 that performs ultrasonic treatment or by the person administering the treatment.

Figure 9C:
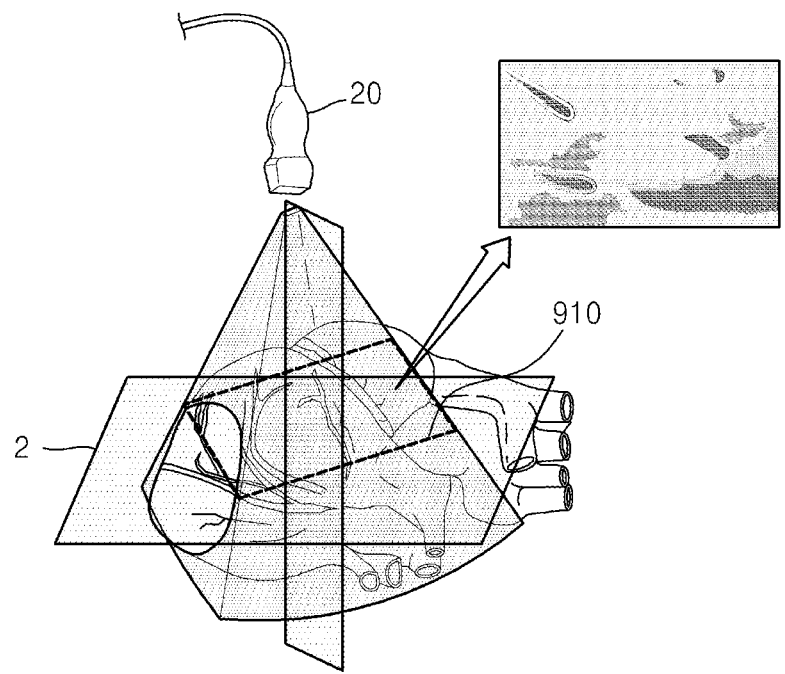

The extraction unit 603 extracts a region corresponding to the plane of interest from three-dimensional volume data. Here, the extracted region is plane data. As illustrated in FIG. 9C, if the plane of interest 2 is set, the region 910 for an organ is extracted from three-dimensional volume data.

Figure 9D:
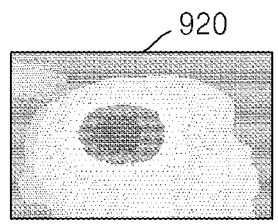

The temperature image generation unit 604 generates a temperature image using frame images acquired by irradiating ultrasonic waves for diagnosis. The temperature image for the extracted region 910 is generated as illustrated in FIG. 9D. As explained with reference to FIG. 5, temperature parameters are extracted using the reference frame that is a frame image acquired before irradiating ultrasonic waves for treatment onto the extracted region 910, and the current frame that is the frame image acquired while or after irradiating the ultrasonic waves for treatment. The reference frame and the current frame is used to generate a temperature image for the extracted region 910.

Figure 9E:
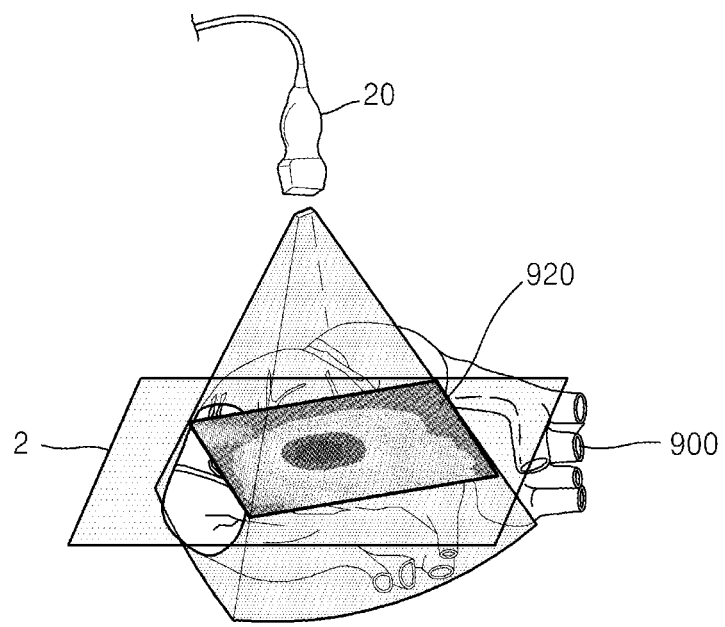

The display controller 605 displays a temperature image generated by the temperature image generation unit 604 on three-dimensional volume data. As illustrated in FIG. 9E, the generated temperature image 920 is displayed on the plane of interest 2 of an organ 900 shown as three-dimensional volume data.

Figure 7:
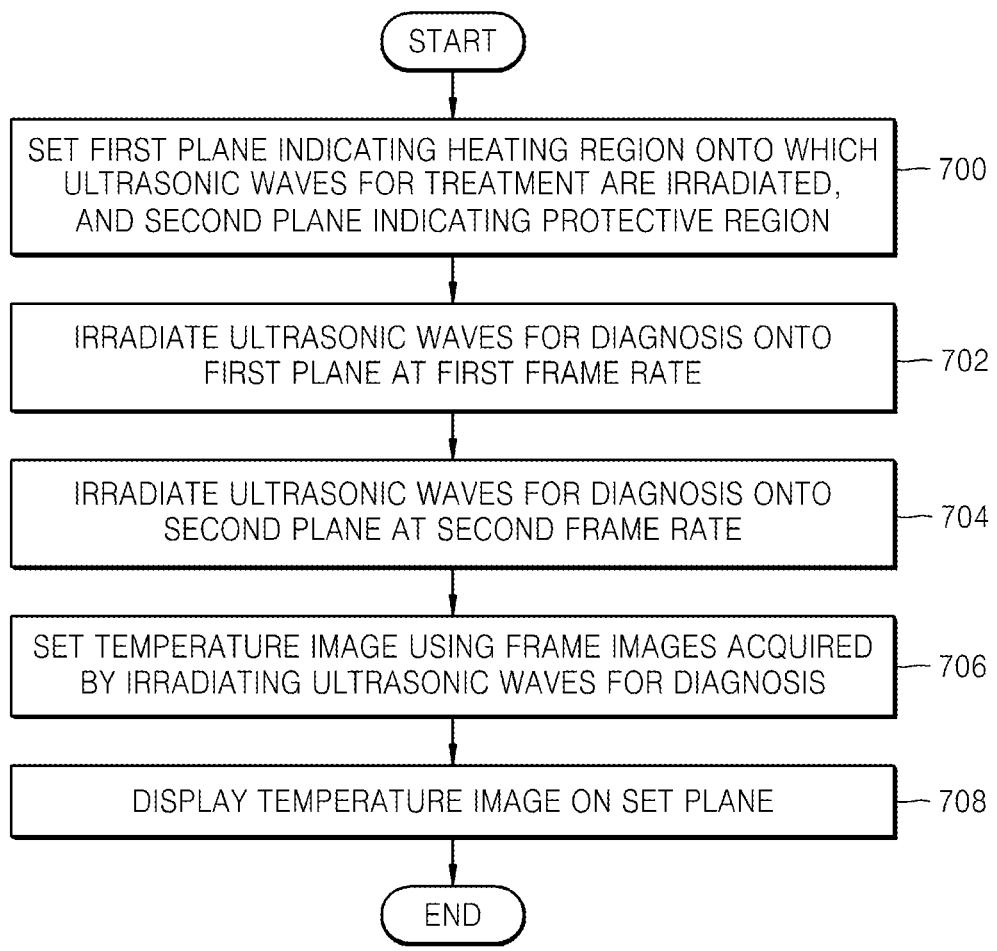
FIG. 7 is a diagram illustrating an example of a method of generating a temperature image.

FIG. 7 is a diagram illustrating an example of a method of generating a temperature image. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. The description of FIGS. 1-6 is also applicable to FIG. 7, and thus will not be repeated here.

Referring to FIG. 7, in 700, a first plane and second plane are set. The first plane represents the heating region where ultrasonic waves for treatment are irradiated and the second plane represents the protective region. The heating region is a region where ultrasonic waves for treatment are irradiated, and the protective region is a region around the heating region. The first plane and the second plane may be automatically set by an ultrasonic system that performs ultrasonic treatment or may be set by the person administering the treatment.

In 702, ultrasonic waves for diagnosis are irradiated onto the first plane at the first frame rate. In 704, ultrasonic waves for diagnosis are irradiated onto the second plane at the second frame rate. The first frame rate is higher than the second frame rate. Greater number of frames of images are acquired by irradiating ultrasonic waves for diagnosis at a high frame rate on the heating region having a larger temperature change before and after irradiation of ultrasonic waves for treatment. Lesser number of frames of images are acquired by irradiating ultrasonic waves for diagnosis at a low frame rate onto the protective region having a smaller temperature change before and after irradiation of ultrasonic waves for treatment.

In 706, a temperature image is generated using frame images acquired by irradiating ultrasonic waves for diagnosis. The temperature image is generated by extracting temperature parameters using the reference frame that is the frame image acquired before irradiating the ultrasonic waves for treatment and the current frame image that is acquired while or after irradiating the ultrasonic waves for treatment.

In 708, the temperature image generated in 706 is displayed on the plane set in 700. Here, the temperature image may be a temperature image for the current frame, and may include one or more of an image displaying a physical quantity proportional to the temperature, an image indicating the temperature change of the observed part shown on the current frame relative to the observed part shown on the reference frame, and an image indicating the absolute temperature value of the observed part shown on the current frame.

Figure 8:
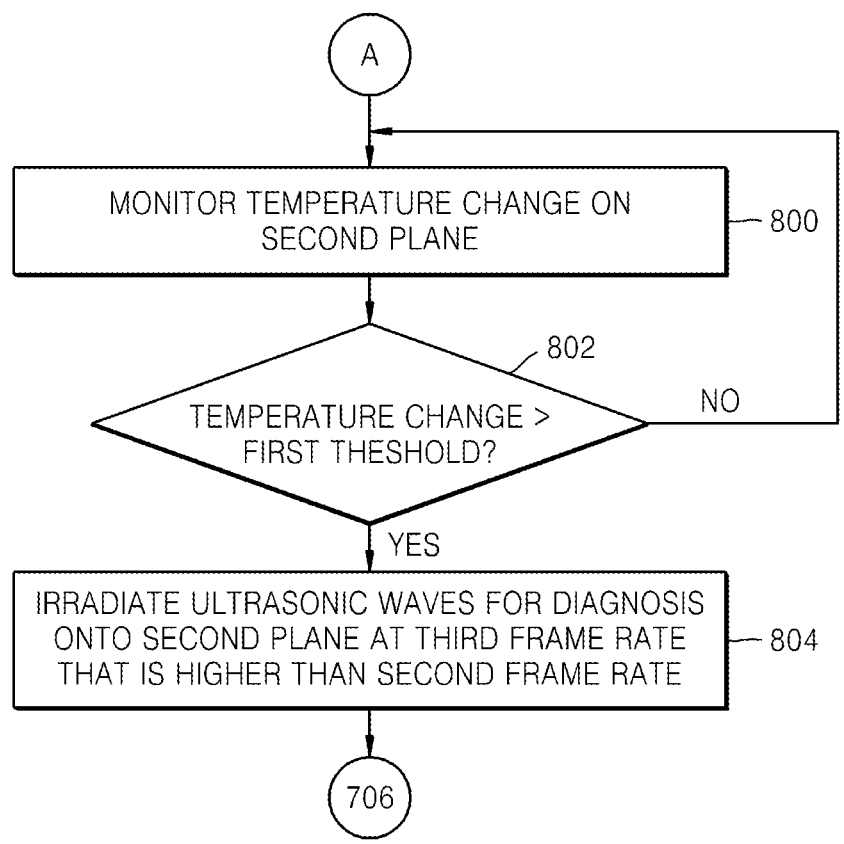
FIG. 8 is a diagram illustrating an example of a method of generating a temperature image.

FIG. 8 is a diagram illustrating an example of a method of generating a temperature image. The operations in FIG. 8 may be performed in the sequence and manner as shown, although the order of some operations may be changed or some of the operations omitted without departing from the spirit and scope of the illustrative examples described. Many of the operations shown in FIG. 8 may be performed in parallel or concurrently. The description of FIGS. 1-7 is also applicable to FIG. 8, and thus will not be repeated here.

Referring to FIG. 8, in 800, the temperature change of the second plane is monitored. The temperature image indicating the temperature change of the second plane is monitored. For example, the temperature change may be monitored through the temperature image corresponding to the second plane or the region set as the protective region.

In 802, if the temperature change on the second plane is greater than a threshold, the ultrasound waves for diagnosis are irradiated onto the second plane at the third frame rate that is higher than the second frame rate in 804, and the process moves to 706 of FIG. 7. In the case where the temperature of the region set as the protective region suddenly increases due to the ultrasonic treatment, the temperature change in the protective region needs to be more carefully observed. Hence, many frame images may be acquired by increasing the observation rate of the ultrasound waves for diagnosis for observation of the protective region to generate the temperature image.

Figure 10:
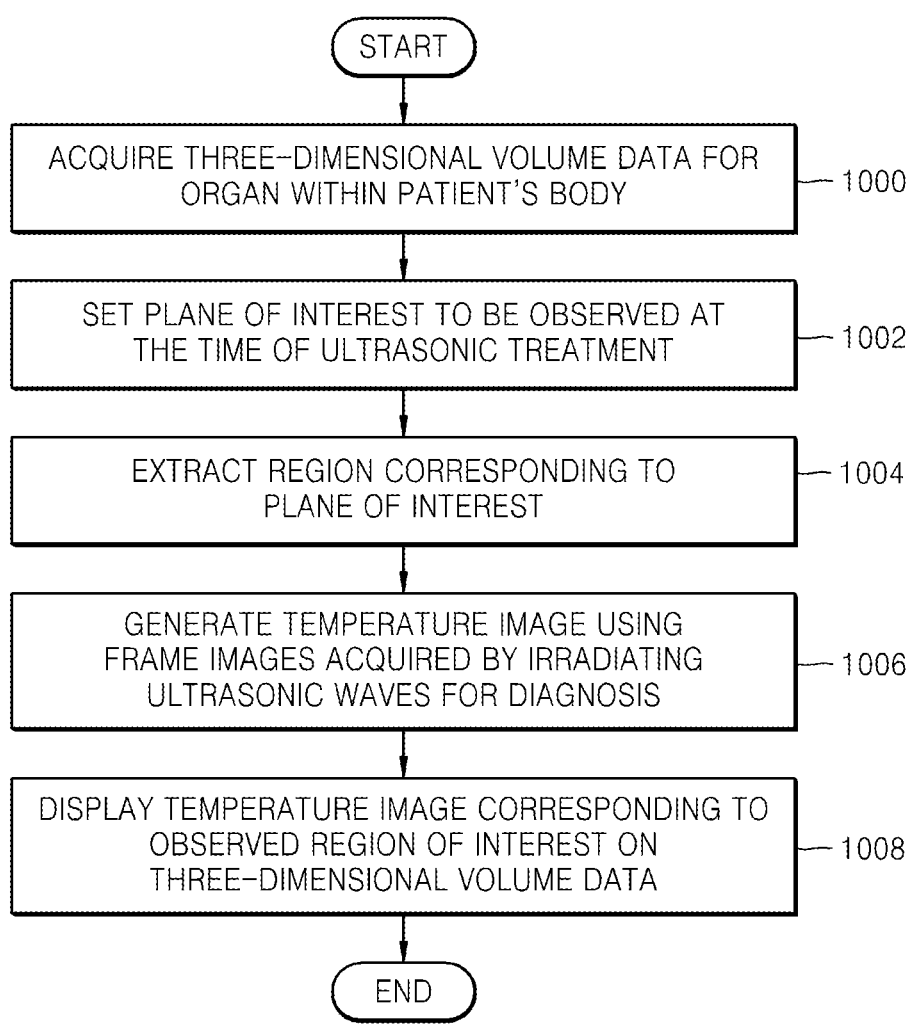
FIG. 10 is a diagram illustrating a method of generating a temperature image.

FIG. 10 is a diagram illustrating an example of a method of generating a temperature image. The operations in FIG. 10 may be performed in the sequence and manner as shown, although the order of some operations may be changed or some of the operations omitted without departing from the spirit and scope of the illustrative examples described. Many of the operations shown in FIG. 10 may be performed in parallel or concurrently. The description of FIGS. 1-9E is also applicable to FIG. 10, and thus will not be repeated here.

Referring to FIG. 10, in 1000, three-dimensional volume data for an organ in a patient's body is acquired. Here, the three-dimensional volume data may be an image captured by a medical expert for patient diagnosis in order to analyze the shape, size, or other features of an organ of a patient treated by ultrasonic waves. For example, a three-dimensional image may be a computed tomography (CT), magnetic resonance (MR), or ultrasonic image. Further, a plurality of two-dimensional images may be input to reconfigure three-dimensional volume data.

In 1002, the plane of interest to be observed at the time of ultrasonic treatment is set. Furthermore, a plurality of planes of interest may be set on the three-dimensional data.

In 1004, the region corresponding to the plane of interest or data regarding the region is extracted. Data corresponding to the plane of interest set on three-dimensional volume data is extracted.

In 1006, a temperature image is generated using frame images acquired by irradiating ultrasonic waves for diagnosis. The acquired frame images are the reference frame image acquired by irradiating ultrasound waves for diagnosis before irradiating ultrasound waves for treatment and the current frame image are acquired by irradiating the ultrasound waves for diagnosis while or after irradiating the ultrasound waves for treatment. Temperature parameters are extracted by comparing the reference frame image with the current frame image, and the temperature image of the current frame is generated based on the extracted temperature parameters. The methods of generating the temperature image may include a CBE scheme, an ES scheme and a scheme of calculating the B/A change, and a combination of these schemes.

In 1008, a temperature image corresponding to an observed region of interest is displayed on the three-dimensional data. According to the one or more of the examples described above, three-dimensional temperature monitoring may be performed in real time by observing an ultrasound-irradiated surface corresponding to a treatment region with high temperature variation at a high frame rate and observing a ultrasound-irradiated surface corresponding to a protective region without high temperature variation at a low frame rate.

Furthermore, according to the one or more of the examples described above, the temperature of a desired plane may be observed, and the number of calculations needed to generate a temperature image may be reduced by extracting a plurality of plane of interest data from three-dimensional volume data, and generating a temperature image using the extracted region. The three-dimensional temperature monitoring may be performed in real time by observing an ultrasound-irradiated surface corresponding to a treatment region with high temperature variation at a high frame rate and observing an ultrasound-irradiated surface corresponding to a protective region without high temperature variation at a low frame rate.

The processes, functions, and methods described above including a method for beamforming can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

All documents cited in the above description, including published documents, patent applications, and patents, may be incorporated herein in their entirety by reference in the same manner as when each cited document is separately and specifically incorporated or incorporated in its entirety.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of generating a temperature image during ultrasonic treatment, the method comprising:
   setting a first plane to indicate a heating region of a body where ultrasonic waves for treatment are irradiated, and setting a second plane to indicate a protective region around the heating region, wherein an intersection of the first and second planes forms a line along an irradiation portion of an ultrasound diagnosis device;
   irradiating the first plane with ultrasonic waves for diagnosis at a first frame rate, from the irradiation portion of the ultrasound diagnosis device, and irradiating the second plane with the ultrasonic waves for diagnosis at a second frame rate, from the irradiation portion of the ultrasound diagnosis device, wherein the second frame rate is lower than the first frame rate; and
   generating the temperature image by using frame images acquired as a result of irradiating the first and second planes with ultrasonic waves for diagnosis.

2. The method of claim 1, wherein the generating of the temperature image comprises:

generating the temperature image, by comparing a reference frame indicating a frame image acquired by irradiating the first and second planes with ultrasonic waves for diagnosis, with a current frame indicating a frame image acquired while or after irradiating the first and second planes with ultrasonic waves for treatment.

3. The method of claim 1, further comprising:
displaying the generated temperature image on a set plane that intersects the first plane and the second plane.

4. The method of claim 1, wherein the irradiating of the ultrasonic waves-for diagnosis, comprises:
time-dividing and irradiating the first plane and the second plane with the ultrasonic waves for diagnosis.

5. The method of claim 1, wherein the ultrasonic waves for diagnosis are irradiated onto the second plane at a third frame rate that is higher than the second frame rate, in response to a temperature change on the second plane being greater than a threshold.

6. The method of claim 1, further comprising:
acquiring three-dimensional volume data for an organ within a body;
setting a plane of interest to be observed during ultrasonic treatment; and
extracting, from the three-dimensional volume data, an extracted region of the body corresponding to the plane of interest,
wherein the first plane and the second plane are set on the extracted region of the body.

7. The method of claim 6, wherein the temperature image corresponding to the plane of interest is displayed on the three-dimensional volume data.

8. The method of claim 6, wherein setting the plane of interest comprises:
setting a plurality of planes of interest to be observed during ultrasonic treatment.

9. The method of claim 1, wherein the ultrasonic waves for treatment and the ultrasonic waves for diagnosis are irradiated from a single transducer of the irradiation portion of the ultrasound diagnosis device.

10. A method of generating a temperature image during ultrasonic treatment, the method comprising:
acquiring three-dimensional volume data for an organ within a body;
setting a plane of interest to be observed at the time of the ultrasonic treatment;
extracting, from the three-dimensional volume data, a region of the body corresponding to the plane of interest; and
generating the temperature image, by using frame images acquired as a result of irradiating, from an irradiation portion of an ultrasound diagnosis device, ultrasonic waves for diagnosis on the plane of interest, wherein the plane of interest forms a line along the irradiation portion of the ultrasound diagnosis device.

11. The method of claim 10, further comprising:
displaying the temperature image corresponding to the plane of interest on the three-dimensional volume data.

12. An apparatus for generating a temperature image during ultrasonic treatment, the apparatus comprising:
a region setter configured to set a first plane to indicate a heating region of a body where ultrasonic waves for treatment are irradiated, and to set a second plane to indicate a protective region of the body, around the heating region, wherein an intersection of the first and second planes forms a line along an irradiation portion of an ultrasound diagnosis device;

an irradiation controller configured to irradiate the first plane with ultrasonic waves for diagnosis at a first frame rate, from the irradiation portion of the ultrasound diagnosis device, and to irradiate the second plane with the ultrasonic waves for diagnosis at a second frame rate, from the irradiation portion of the ultrasound diagnosis device, wherein the second frame rate is lower than the first frame rate; and a temperature image generator configured to generate the temperature image, by using frame images acquired as a result of irradiating the first and second planes with ultrasonic waves for diagnosis.

13. The apparatus of claim 12, where the temperature image generator is further configured to generate the temperature image, by comparing a reference frame to indicate a frame image acquired by irradiating the first and second planes with ultrasonic waves for diagnosis, with a current frame to indicate a frame image acquired while or after irradiating the first and second planes with ultrasonic waves for treatment.

14. The apparatus of claim 12, further comprising:
a display controller configured to display the generated temperature image on a set plane that intersects the first plane and the second plane.

15. The method of claim 12, wherein the irradiation controller is configured to time-divide and irradiate the first plane and the second plane with the ultrasonic waves for diagnosis.

16. The apparatus of claim 12, wherein the irradiation controller is further configured to irradiate the second plane with the ultrasonic waves for diagnosis at a third frame rate that is higher than the second frame rate, in response to a temperature change on the second plane being greater than a threshold.

17. An apparatus for generating a temperature image during ultrasonic treatment, the apparatus comprising:
a three-dimensional volume data acquirer configured to acquire three-dimensional volume data for an organ within a body;
a plane of interest setter configured to set a plane of interest intended to be observed at the time of the ultrasonic treatment;
an extractor configured to extract, from the three-dimensional volume data, a region of the body corresponding to the set plane of interest; and
a temperature image generator configured to generate the temperature image, by using frame images acquired as a result of irradiating, from an irradiation portion of an ultrasound diagnosis device, the ultrasonic waves for diagnosis on the plane of interest, wherein the plane of interest forms a line along the irradiation portion of the ultrasound diagnosis device.

18. The method of claim 17, further comprising:
a display controller configured to display the temperature image corresponding to the plane of interest on the three-dimensional volume data.

19. An ultrasonic apparatus including a temperature image generation device configured to produce a temperature image during ultrasonic treatment, the ultrasonic apparatus comprising:
an ultrasonic treatment device configured to generate ultrasonic waves to irradiate a treatment region of an organ in a body, and to heat a lesion for treatment;
an ultrasound diagnosis device, including an irradiation portion, the ultrasound diagnosis device configured
to generate ultrasound waves to irradiate the treatment region of the body,
to irradiate a region surrounding the treatment region, and
to output reflected waves of the ultrasonic waves for diagnosis; and
the temperature image generation device configured
to set a first plane to indicate a heating region of the body where the ultrasonic waves for treatment are irradiated,
to set a second plane to indicate a protective region around the heating region, wherein an intersection of the first and second planes forms a line along an irradiation portion of an ultrasound diagnosis device,
to irradiate the first plane with the ultrasonic waves at a first frame rate for diagnosis, from the irradiation portion of the ultrasound diagnosis device,
to irradiate the second plane with the ultrasonic waves at a second frame rate, from the irradiation portion of the ultrasound diagnosis device, wherein the second frame rate is lower than the first frame rate, and
to generate the temperature image, by using frame images acquired as a result of reflected waves output by the ultrasonic diagnosis device.

20. The ultrasonic apparatus of claim 19, further comprising:
a display device configured to display the generated temperature image on a set plane that intersects the first plane and the second plane, wherein the display device is controlled by the temperature image generation device.

* * * * *